US00PP15792P3

(12) United States Plant Patent
Beineke

(10) Patent No.: US PP15,792 P3
(45) Date of Patent: Jun. 14, 2005

(54) BLACK WALNUT TREE NAMED 'BEINEKE 8'

(50) Latin Name: *Juglans nigra*
Varietal Denomination: Beineke 8

(75) Inventor: Walter Beineke, West Lafayette, IN (US)

(73) Assignee: American Forestry Technologies, Inc., West Point, IN (US)

( * ) Notice: Subject to any disclaimer, the term of this patent is extended or adjusted under 35 U.S.C. 154(b) by 150 days.

(21) Appl. No.: 10/141,092

(22) Filed: May 8, 2002

(65) Prior Publication Data

US 2003/0213033 P1 Nov. 13, 2003

(51) Int. Cl.[7] ..... A01H 5/00
(52) U.S. Cl. ..... Plt./154
(58) Field of Search ..... Plt./154

(56) References Cited

U.S. PATENT DOCUMENTS

| | | | |
|---|---|---|---|
| PP4,132 | P | 10/1977 | Genn |
| PP4,388 | P | 2/1979 | Forde |
| PP4,389 | P | 2/1979 | Forde |
| PP4,405 | P | 4/1979 | Forde |
| PP4,542 | P | 6/1980 | Beineke |
| PP4,543 | P | 6/1980 | Beineke |
| PP4,614 | P | 1/1981 | Beineke |
| PP4,954 | P | 11/1982 | Beineke |
| PP4,955 | P | 11/1982 | Beineke |
| PP4,964 | P | 12/1982 | Beineke |
| PP4,966 | P | 12/1982 | Beineke |
| PP4,968 | P | 12/1982 | Beineke |
| PP4,971 | P | 1/1983 | Beineke |
| PP6,973 | P | 8/1989 | Madison |
| PP9,906 | P | 6/1997 | Jones |
| PP9,924 | P | 6/1997 | Jones |
| PP9,925 | P | 6/1997 | Jones |

OTHER PUBLICATIONS

Appleton, Bonnie, et al. (2000) "Trees for problem Landscape Sites—The Walnut Tree: Allelopathic Effects and Tolerant Plants" *Virginia State University* Publication No. 430–021.
Beineke, Walter F. (1989) "Twenty Years of Black Walnut Genetic Improvement at Purdue University" *NJAF* 6:68–71.
Coladonato, Milo (1991) "*Juglans Nigra*" 1–11.
Esser, Lora. (1993) "*Juglans Californica*" 1–11.
Pavek, Diane S. (1993) "*Juglans Major*" 1–13.
Tirmenstein, D.S. (1990) "*Juglans Microcarpa*" 1–11.
Website: http://www.treeguide.com/naspecies.asp?treeid=junigrl: printed Aug. 30, 2001: pp. 1–11.
Website: http://virual.clemson.edu/groups/FieldOps/Cgs/walnut.htm: printed Aug. 30, 2001: pp. 1–3.
Woeste, K., et al. (2002) "Thirty Polymorphic Nuclear Microsatellite Loci From Black Walnut" *The Journal of Heredity* 93(1):58–60.

*Primary Examiner*—Kent Bell
(74) *Attorney, Agent, or Firm*—Alice O. Martin; Barnes & Thornburg

(57) ABSTRACT

A new and distinct cultivar of black walnut tree (*Juglans nigra* L.) which is distinctly characterized by rapid growth rate, fairly strong central stem tendency, thereby producing good timber qualities. The new variety has good nut bearing qualities. Nut crops are abundant and annual. This new variety of black walnut tree (*Juglans nigra* L.) was discovered by the applicant near West Lafayette, Ind. in a black walnut planting of seedling progeny from a previously selected tree for outstanding timber producing potential. This selection, has been designated as BW420, a seedling progeny of BW 205 (unpatented) which is a progeny of BW 97 (unpatented) in records maintained by the applicant on the performance of the selection and grafts made from the selection will be known henceforth as 'Beineke 8'.

3 Drawing Sheets

Latin name of the genus and species: *Juglans nigra* L.

BACKGROUND OF THE INVENTION

A new variety of black walnut tree (*Juglans nigra* L.) was discovered by the applicant near West Lafayette, Ind. in a black walnut planting of seedling progeny from previously selected trees for outstanding timber producing potential. This selection has been designated as BW420, a seedling progeny of BW 205 (unpatented) which is a progeny of BW 97 (unpatented) in records maintained by the applicant on the performance of the selection and grafts made from the selection and will be known henceforth as 'Beineke 8'. The male parent is unknown, as is generally the case with black walnut trees (Beineke, 1989).

A new and distinct cultivar of black walnut tree (*Juglans nigra* L.) is distinctly characterized by rapid growth rate and fairly strong central stem tendency, thereby producing good timber qualities, the trait of commercial interest. 'Beineke 8' was 22 years old when described at a location near West Lafayette, Ind.

After the original clone was selected, and assigned an identity number of BW420 the aforesaid tree was reproduced by collecting scions from it and grafting these onto common black walnut rootstocks at American Forestry Technologies, Inc., West Point, Ind. These asexual reproductions ran true to the originally discovered tree and to each other in all respects. Because neither BW 97 nor BW 205 were planted on the same site and were no longer available, further comparisons with the parent tree were not possible.

SUMMARY OF THE INVENTION

Color values used were from the Munsell Color Chart for Plant Tissues. However, color is too dependent on weather conditions and fertilization to be consistent or distinctive. For example, leaves can be made a deeper green by applying nitrogen. Walnut tree leaves turn yellow as the season progresses, especially if there is a lack of rainfall. As black walnut meats dry, they become darker. Simply being on the ground for a week causes the outer shell to darken. Bark color involves many shades of gray through brown and black.

'Beineke 8' is hardy in zones 4, 5, 6, 7, and 8.

BOTANICAL DESCRIPTION OF THE PLANT

The botanical details of this new and distinct variety of walnut tree are as follows:

Tree:

*Size.*—Large, 67 ft. at 22 years; crown diameter is 26 ft.

*Vigor.*—Vigorous.

*Growth rate.*—Very rapid, 20% larger in diameter than the average of Purdue 1 (U.S. Plant Pat. No. 4,543) grafts, respectively, planted the same year on the same land. Diameter growth rate (at 4½ feet above the ground) averages 0.546 inches per year, over 22 years about 12 inches.

*Form.*—Good timber form, not as good as Purdue 1, (U.S. Plant Pat. No. 4,543) 34% poorer than average of the entire planting, on a rating scale of 1 (excellent) to 5 (very poor) — 'Beineke 8' averages 2. 33% straighter than the first generation of the parent tree, BW 97 and the same straightness as second generation parent tree BW 205. Stem form was obtained by subjectively rating the straightness of the main stem on a scale of 1 to 5 with 1 representing a perfectly straight stem; 2, slight crook or deviation of the central stem; 3, about average straightness; 4, several severe crooks or a single fork; and 5, a very crooked, forked and/or leaning central stem. The trees of the present invention are grown in plantations, not open fields (not natural stands). In plantations, trees are upright and have no distinctive or characteristic crown shape because all branches are seeking to grow upwards.

Branches:

Diameter depends on age and size of tree, varies from ½" to 12", bark color varies from grays to browns.

Leaves:

*Compound leaves.*—Size — Much shorter than average; average length — 11.83".

*Leaflets.*—Size — Average; average length — 3.83"; average leaf width — 3.10"; average number of leaflets — 15.0 — lanceolate; acutely pointed; rounded; petioles are short.

*Thickness.*—Thin; Texture — smooth; Margin — serrated; Color — Topside — dark green, 2.5 G 4/4 on the Munsell Color Chart for Plant Tissues; Underside — light green, about 5 GY 5/4 on the Munsell Color Chart for Plant Tissues.

*Anthracnose resistance.*—Good.

Nut:

*Size.*—Medium; average length — 1.22"; average diameter in suture plane — 1.20"; average diameter cheek to cheek — 1.42".

*Uniformity of size.*—Not much variation.

Figure 1:
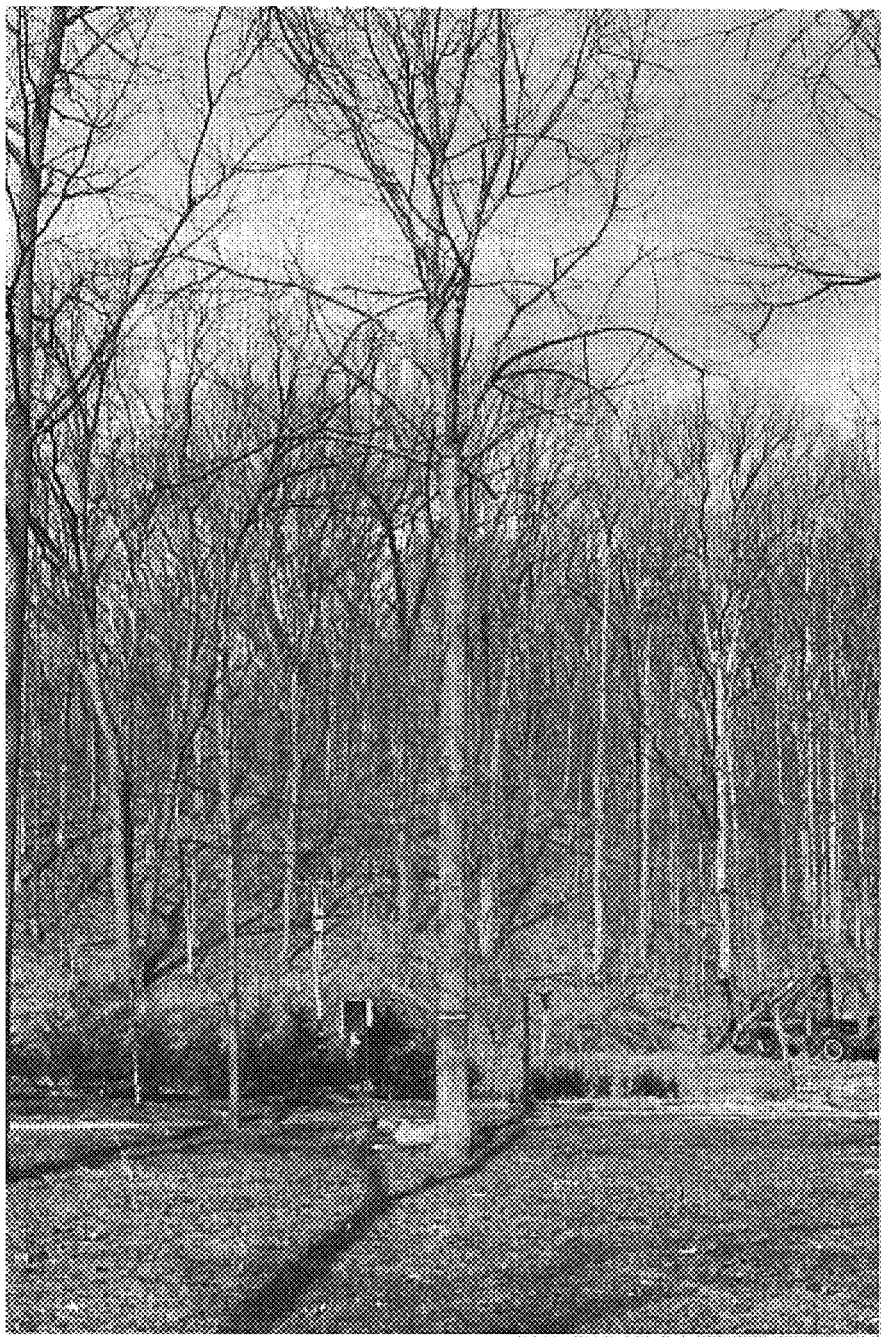
FIG. 1 is a photograph showing the timber form of 'Beineke 8'.
Figure 2:
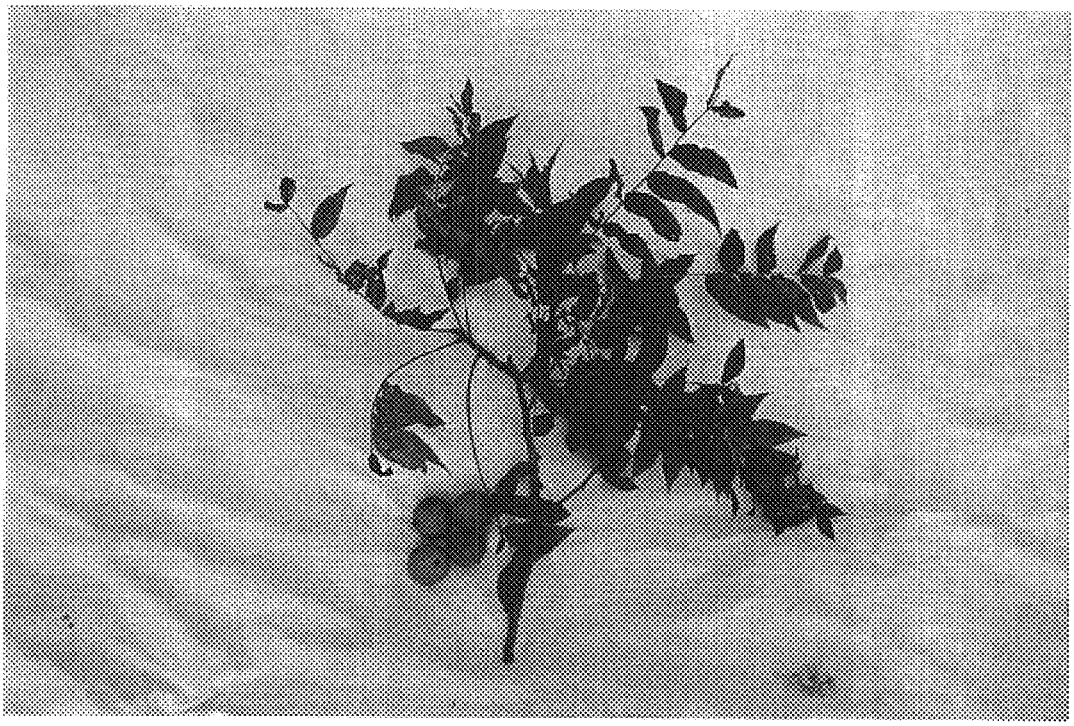
FIG. 2 is a photograph showing the leaves of 'Beineke 8'.
Figure 3:
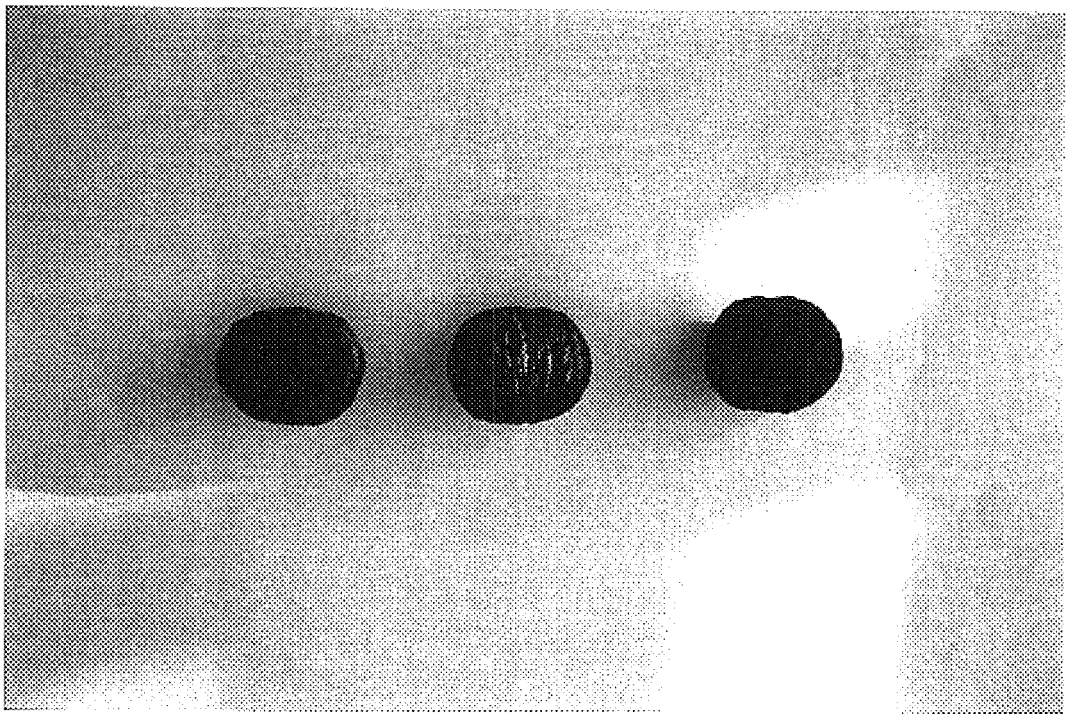
FIG. 3 is a photograph showing the nuts of 'Beineke 8'.

*Form.*—Rounded; flattened in suture plane; see FIG. 3.

*Blossom end.*—Flattened.

*Basal end.*—Rounded.

*Thickness of shell.*—Very thick.

*Ridges.*—Rounded off; not sharp.

*Color.*—Mottled, 5 YR 3/2 and 2/5 YR 3/4 on the Munsell Color Chart for Plant Tissues.

Flowering habit:

*Age at which trees start producing catkins.*—Early. It takes about 4–5 years to flower but the flower number varies with the age of the tree.

*Number of catkins produced.*—Abundant.

*Age at which tree starts producing pistillate flowers.*—Early, 4–5 years.

*Number of pistillate flowers produced by young trees.*—Abundant.

*Number of pistillate flowers produced by mature trees.*—Abundant.

*Lateral shoots producing pistillate flowers.*—None.

*Number of pistillate flowers per inflorescence.*—2 to 6.

Flower season:

Flowers typically in May in Indiana. There are probably 1 - million pollen per catkin. Female flowers are about 1/16" long and grow to two "pollen pick up points" which subsequently break apart. Pollen exits as "dust" which is not feasible to quantitate.

Nut crop:

*Bearing.*—Annual.

*Productivity.*—Heavy.

*Ripening period.*—Very early.

*Evenness of maturity* (*period between first and last nuts are ready for harvest*).—Uneven.

*Quality.*—Good.

*Distribution of nuts on tree.*—Throughout.

*Color.*—Mottled, 5YR.

GENETIC METHOD OF IDENTIFICATION

DNA "fingerprint" for identification of 'Beineke 8:'

DNA was isolated from the leaves of 'Beineke 8.' For purposes of DNA fingerprinting, nine highly polymorphic loci from a suite of microsatellites developed by Woeste et al. (2002) were chosen. Microsatellites sizes were checked against previously published standards and verified by a second independent analysis. The "fingerprint" is the collection of microsatellite allele sizes at each locus for 'Beineke 8.'

DNA was isolated from the leaves of 10 black walnut trees obtained from Walter Beineke using CTAB extraction buffer (50 mM TRIS-HCL, pH 8.0, 20 mM EDTA, pH 8.0, 0.7 M NaCl, 0.4 M LiCl, 2% SDS, 2% TAB, nd 1% PVP). After isolation the DNA from each tree was quantified and diluted with nanopure distilled water to a final concentration of 5 ng/$\mu$L. The samples were stored in 96-well plates at 20° C.

For purposes of DNA fingerprinting, nine highly polymorphic loci from a suite of microsatellites developed by Woeste et al. (2002) were chosen. Amplification of each locus was performed with an MJ Research Tetrad Thermocycler (Waltham, Mass.) using 10 $\mu$L reactions in 96-well plates. The PCR reaction mix contained 2 $\mu$L of the aforementioned black walnut DNA, 5 $\mu$L Sigma Taq ReadyMix (Sigma Aldrich, St. Louis, Mo.), 0.4 μL of a 20 pmol mixture of forward and reverse fluorescence labeled primer, and 3 μL PCR grade water supplied with the Sigma ReadyMix. PCR amplification was for 30 cycles of 94° C. for 20 sec, 55° C. for 30 sec, and 72° C. for 1 min. All primers were annealed at 55° C. The products were then held at 4° C. until aliquots could be loaded into 6% Long Ranger (polyacrylamide) denaturing gels (BMA, Rockland, Me.). For each individual 0.5 μL PCR product was added to 0.75 μL blue dextran and 0.25 μL of CXR 350 bp Ladder Standard (Promega, Fitchburg Center, Wis.) in a new 96-well 1 late. The samples were denatured for 2 min at 95° C. and located onto a CAL96 96-well laminated membrane comb (The Gel Company, San Francisco, Calif.). Electrophoresis was at 3,000 V, 60 mA, 200 Watts, 50° C. for hours using an ABI377 (Perkin Elmer) with 36 cm plates and 0.2 mm spacers. The resulting data was analyzed using ABI's GeneScan 3.1.2 and Genotyper 2.5 (Perkin Elmer). Microsatellite sizes were checked against previously published standards and verified by a second independent analysis. The "fingerprint" is the collection of microsatellite allele sizes at each locus for each tree.

Primer Sequences

| Locus | Forward | Reverse |
|---|---|---|
| WGA2 | GACGACGAAGGTGTACGGAT (SEQ ID NO:1) | GTACGGCTCTCCTTGCAGTC (SEQ ID NO:10) |
| WGA6 | CCATGAAACTTCATGCGTTG (SEQ ID NO:2) | CATCCCAAGCGAAGGTTG (SEQ ID NO:11) |
| WGA24 | TCCCCCTGAAATCTTCTCCT (SEQ ID NO:3) | TTCTCGTGGTGCTTGTTGAG (SEQ ID NO:12) |
| WGA32 | CTCGGTAAGCCACACCAATT (SEQ ID NO:4) | ACGGGCAGTGTATGCATGTA (SEQ ID NO:13) |
| WG33 | TGGTCTGCGAAGACACTGTC (SEQ ID NO:5) | GGTTCGTCGTTTGTTGACCT (SEQ ID NO:14) |

-continued

Primer Sequences

| Locus | Forward | Reverse |
|---|---|---|
| WGA86 | ATGCCTCATCTCCATTCTGG (SEQ ID NO:6) | TGAGTGGCAATCACAAGGAA (SEQ ID NO:15) |
| WGA89 | ACCCATCTTTCACGTGTGTG (SEQ ID NO:7) | TGCCTAATTAGCAATTTCCA (SEQ ID NO:16) |
| WGA90 | CTTGTAATCGCCCTCTGCTC (SEQ ID NO:8) | TACCTGCAACCCGTTACACA (SEQ ID NO:17) |
| WGA97 | GGAGAGGAAAGGAATCCAAA (SEQ ID NO:9) | TTGAACAAAAGGCCGTTTTC (SEQ ID NO:18) |

The best interpretation of the current data indicates that the probability that any other black walnut tree would have the collection of microsatellite allele sizes listed below is less than 1 in $10^{-17}$.

Sizes (bp) of microsatellites at 9 loci used to fingerprint 'Beineke 8' (2 alleles at each locus)

| WGA2 | | WGA6 | | WGA24 | | WGA32 | | WGA90 | |
|---|---|---|---|---|---|---|---|---|---|
| 132 | 164 | 140 | 158 | 234 | 242 | 181 | 187 | 152 | 156 |
| WGA86 | | WGA97 | | WGA33 | | WGA89 | | | |
| 216 | 238 | 155 | 159 | 232 | 232 | 201 | 213 | | |

DOCUMENTS CITED

Beineke, Walter F. (1989) Twenty years of black walnut genetic improvement at Purdue University *North. J. Appl.* For. 6:68–71.

Woeste, K., Burns, R., Rhodes, O., and Michler, C. (2002) Thirty polymorphic nuclear microsatellite loci from black walnut. *Journal of Heredity,* 93(1):58–60.

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1

gacgacgaag gtgtacggat                                                20


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
```

-continued ccatgaaact tcatgcgttg 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3 tccccctgaa atcttctcct 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4 ctcggtaagc cacaccaatt 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5 tggtctgcga agacactgtc 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6 atgcctcatc tccattctgg 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7 acccatcttt cacgtgtgtg 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8 cttgtaatcg ccctctgctc 20

<210> SEQ ID NO 9
<211> LENGTH: 20
<212> TYPE: DNA

-continued

<213> ORGANISM: Artificial Sequence
<220> FEATURE:
<223> OTHER INFORMATION: Description of Artificial Sequence: Primer

<400> SEQUENCE: 9 ggagaggaaa ggaatccaaa 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10 gtacggctct ccttgcagtc 20

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 11 catcccaagc gaaggttg 18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12 ttctcgtggt gcttgttgag 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13 acgggcagtg tatgcatgta 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14 ggttcgtcgt ttgttgacct 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15

-continued

```
tgagtggcaa tcacaaggaa                                                20


<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16

tgcctaatta gcaatttcca                                                20


<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17

tacctgcaac ccgttacaca                                                20


<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 18

ttgaacaaaa ggccgttttc                                                20
```

I claim:

1. A new and distinct variety of black walnut tree named 'Beineke 8' substantially as illustrated and described, which has good timber quality, is flat growing, has fairly strong central stem tendency, no sweep, and few crooks.

* * * * *